(12) United States Patent
Ferraresi

(10) Patent No.: US 9,993,616 B2
(45) Date of Patent: Jun. 12, 2018

(54) DEVICE FOR REMOVING A VASCULAR OCCULSION

(71) Applicant: KARDIA S.R.L., Milan (IT)

(72) Inventor: Roberto Ferraresi, Milan (IT)

(73) Assignee: KARDIA S.R.L., Milan (MI) (IT)

( * ) Notice: Subject to any disclaimer, the term of this patent is extended or adjusted under 35 U.S.C. 154(b) by 94 days.

(21) Appl. No.: 14/373,257

(22) PCT Filed: Jan. 16, 2013

(86) PCT No.: PCT/IB2013/050400
§ 371 (c)(1),
(2) Date: Jul. 18, 2014

(87) PCT Pub. No.: WO2013/108192
PCT Pub. Date: Jul. 25, 2013

(65) Prior Publication Data
US 2014/0371758 A1    Dec. 18, 2014

(30) Foreign Application Priority Data
Jan. 18, 2012 (IT) ............. MI2012A000047

(51) Int. Cl.
*A61M 25/01* (2006.01)
*A61M 25/09* (2006.01)
(Continued)

(52) U.S. Cl.
CPC ......... *A61M 25/0127* (2013.01); *A61B 17/22* (2013.01); *A61M 25/09041* (2013.01);
(Continued)

(58) Field of Classification Search
CPC ........... A61B 2017/00469; A61B 2017/22038; A61B 2017/22039; A61B 2017/22042;
(Continued)

(56) References Cited

U.S. PATENT DOCUMENTS 5,624,430 A    4/1997  Eton et al.
5,895,404 A *  4/1999  Ruiz .................. A61B 17/11
                                              600/11
(Continued)

FOREIGN PATENT DOCUMENTS

WO    00/00252 A1    1/2000
WO    00/27312 A1    5/2000

OTHER PUBLICATIONS

The International Search Report for International Application No. PCT/IB2013/050400, five pages, dated May 14, 2013. PCT/ISA/220; PCT/ISA/210.

*Primary Examiner* — Todd J Scherbel
(74) *Attorney, Agent, or Firm* — Vorys, Sater, Seymour & Pease LLP; Ari Zytcer

(57) ABSTRACT

Provided is a device for removing vascular occlusions, including a first guide wire configured to be inserted into a blood vessel so as to be placed in correspondence with the vascular occlusion and having a head including a ferromagnetic material, an emitter configured to emit a magnetic field, a second guide wire configured to permit the emitter to be placed inside the blood vessel in correspondence with the vascular occlusion and on an opposite side with respect to the first guide wire so that the emitter exerts a restoring force on the first guide wire.

7 Claims, 2 Drawing Sheets

(51) Int. Cl.
*A61B 17/22* (2006.01)
*A61B 17/00* (2006.01)

(52) U.S. Cl.
CPC ........... *A61B 2017/00411* (2013.01); *A61B 2017/00734* (2013.01); *A61B 2017/00876* (2013.01); *A61B 2017/22042* (2013.01); *A61B 2017/22094* (2013.01); *A61M 2025/09133* (2013.01); *A61M 2025/09183* (2013.01)

(58) Field of Classification Search
CPC .......... A61B 2017/22094; A61B 2017/22095; A61B 2017/320052; A61B 2017/00876; A61B 17/11–17/1155; A61B 17/22–17/2256; A61B 17/32–17/326; A61B 17/1707; A61B 1/00158
See application file for complete search history.

(56) References Cited

U.S. PATENT DOCUMENTS

| | | | |
|---|---|---|---|
| 6,985,776 B2* | 1/2006 | Kane | A61N 1/056 600/585 |
| 2004/0002714 A1* | 1/2004 | Weiss | A61F 2/07 606/108 |
| 2004/0225233 A1 | 11/2004 | Frankowski et al. | |
| 2007/0208368 A1 | 9/2007 | Katoh et al. | |
| 2012/0197062 A1* | 8/2012 | Requarth | A61B 17/11 600/12 |

* cited by examiner

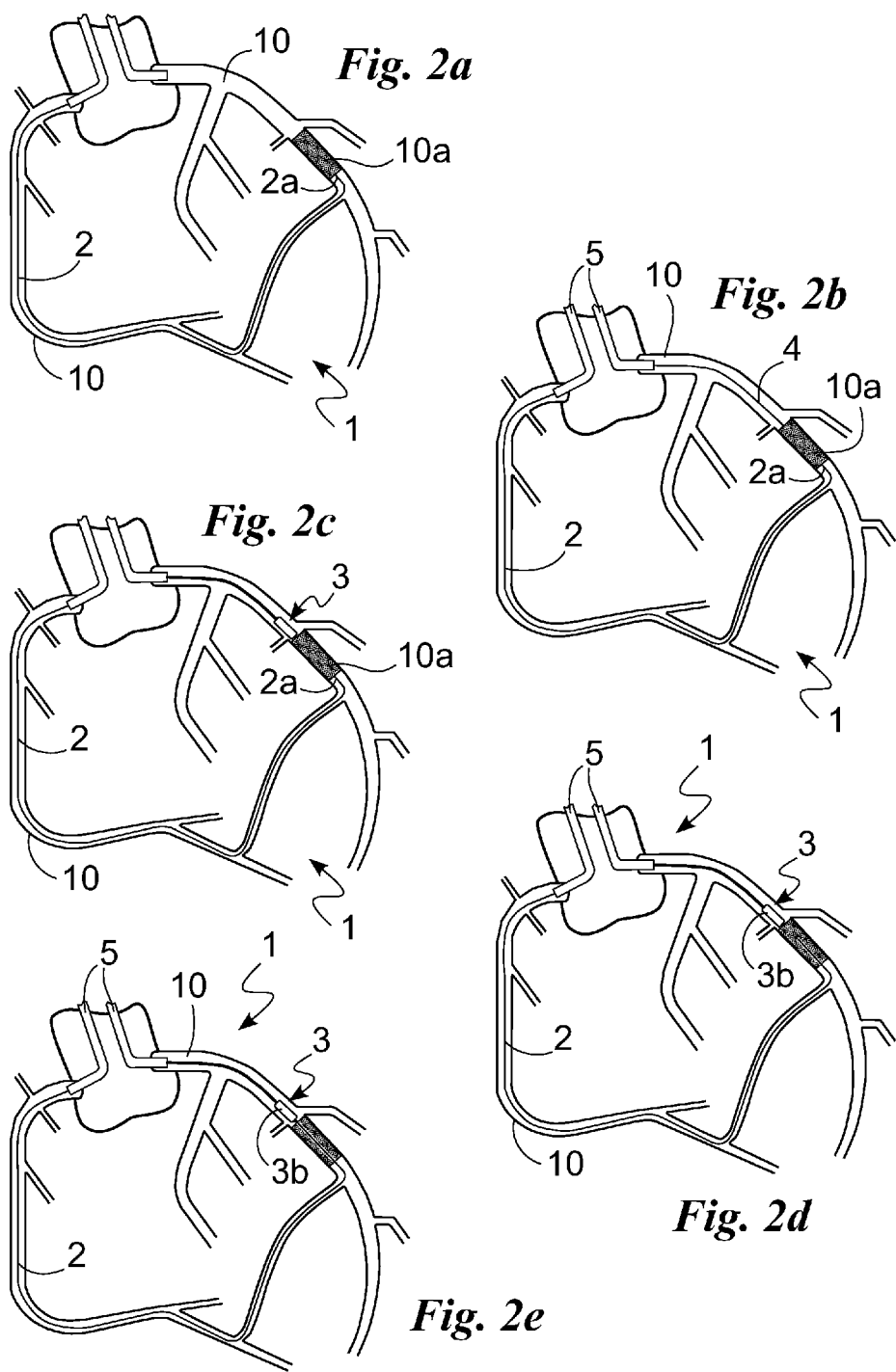

DEVICE FOR REMOVING A VASCULAR OCCULSION

The present invention relates to a device for removing a vascular occlusion of the type as recited in the preamble of Claim 1.

In detail, the invention concerns a device that can be used to remove vascular occlusions and, in particular, chronic occlusions that obstruct the blood flow within an artery or a vein and, thus, prevent the blood from reaching a certain part of the body.

As is known, vascular occlusions are removed by following two distinct approaches, i.e.: an anterograde approach in which the occlusion is treated from upstream, that is to say in correspondence with the part which, according to the direction of the blood flow, is upstream of the occlusion, or, if the attempt to pass the occlusion from anterograde fails, it is possible to attempt to pass the occlusion using a retrograde approach.

With the anterograde approach, the operator injects a radiographic liquid contrast medium into the patient and performs radiography to obtain images of the part of the body concerned, which are displayed on a screen in order to monitor the progress of the entire operation.

At this point, the operator inserts a hollow tube into the artery/vein through which a guide wire is inserted into the artery and positioned upstream of the occlusion. When the guide wire has reached this position, the operator moves the guide wire manually in order to make it pass the occlusion and thus reach the downstream side thereof.

Once the guide wire has passed the occlusion, the operator performs angioplasty or another type of procedure to remove the material occluding the blood vessel in order to open the occluded segment, for example rotational, directional or laser atherectomy, etc.

In detail, the operator slides balloon catheters or other similar devices along the guide wire which, when inflated in correspondence with the occlusion with or without a stent, open the blocked segment to re-establish the normal blood flow inside the vessel.

The anterograde approach is not always effective, since it is sometimes impossible to pass the guide wire through the occlusion to reach the pervious vessel downstream. In these cases the operator may decide to attempt a retrograde approach to pass the occlusion.

As for the anterograde approach described above, the operator injects a contrast medium into the patient and performs radiography to obtain images of the part of the body concerned, and inserts a hollow tube into the artery/vein.

Having performed these operations, the operator inserts the guide wire inside the hollow tube, advances it as far as the downstream side of the occlusion and then advances the guide wire inside the occlusion until it exits the occlusion on the upstream side.

At this point, as with the anterograde approach, the operator performs angioplasty in order to open the occluded segment and re-establish the correct blood flow in the blood vessel.

The prior art described above has several significant drawbacks.

A first important drawback lies in the complexity and length of the operation.

In particular, said complexity is due to the fact that the operator encounters numerous difficulties when advancing the guide wire through the occlusion because, since it protrudes at least partially from the hollow tube, it is substantially free to move in any direction.

This difficulty is worsened by the fact that some sections of the occlusion may be particularly hard and, thus, offer greater resistance to the passage of the guide wire than, for example, the wall of the blood vessel.

For this reason, the operator could inadvertently perforate the blood vessel and thus cause internal lesions and, in some cases, haemorrhages or other serious problems.

Said difficulties in advancing the guide wire could result in said guide wire leaving the true lumen of the blood vessel into the wall thereof, in a space commonly known as the subintimal space, from which it is difficult to re-enter the true lumen of the vessel.

Another drawback lies in the fact that, due to the exposure to radiation and said complexity and the length of the operation, the patient absorbs a large amount of radiation and is therefore exposed to an increased risk of possible damage caused by ionising radiation.

A further drawback lies in the fact that, due to the considerable length of the operation and the need to have the best possible view of the occlusion throughout the entire operation, a large amount of contrast medium has to be injected into the patient, which may have general toxic effects.

Another drawback, which is no less important, lies in the fact that, due to the considerable amount of time required to remove the occlusion, such operations are expensive.

In this situation the technical purpose of the present invention is to develop a device for removing a vascular occlusion able to substantially overcome the inconveniences mentioned above.

Within the sphere of said technical purpose one important aim of the invention is to provide a removal device that is both practical and easy to use.

Another important aim of the invention is to provide a removal device that permits an operation to be performed extremely quickly so that the amount of radiation absorbed by the patient during the operation is reduced.

In particular, an important aim of the invention is to obtain a removal device which requires the use of an extremely small amount of contrast medium.

A further aim is to provide a device that permits the costs of such operation to be reduced.

The technical purpose and specified aims are achieved with a device for removing a vascular occlusion as claimed in the appended claim 1. Preferred embodiments are described in the dependent claims.

The characteristics and advantages of the invention are clearly evident from the following detailed description of a preferred embodiment thereof, with reference to the accompanying drawings, in which:

FIGS. 2a-2e show steps in the use of the removal device according to the invention.

Figure 1A:
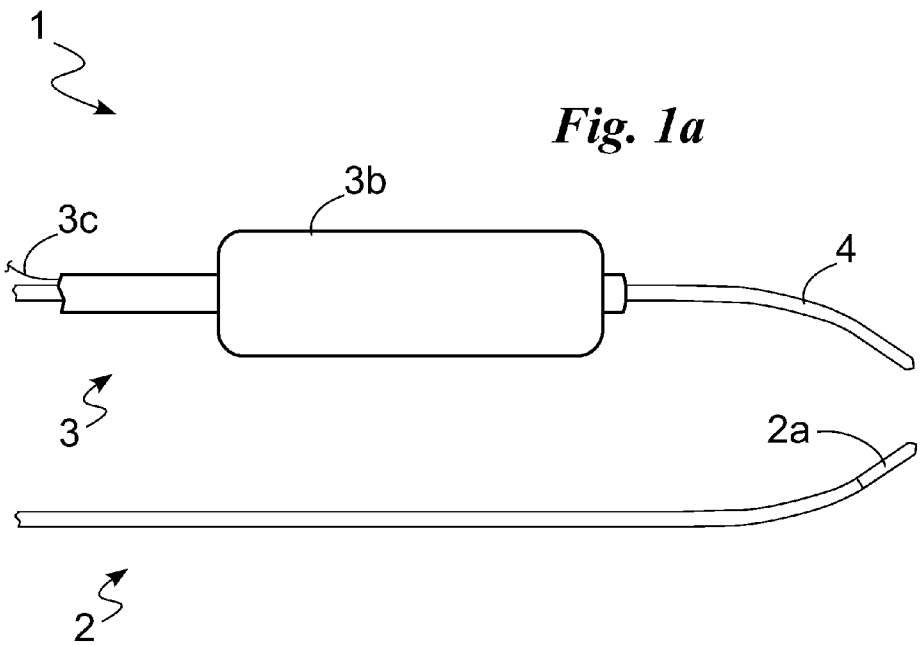
FIG. 1a shows a device for removing a vascular occlusion according to the invention.
Figure 1B:
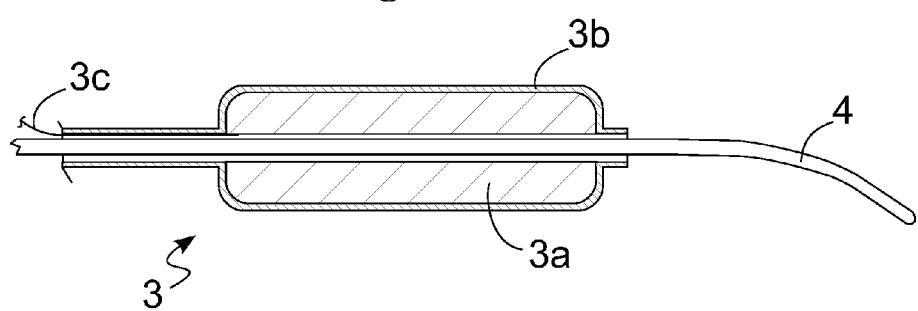
FIG. 1b illustrates a cross-section of a portion of the removal device.

With reference to said drawings, reference numeral 1 globally denotes the device for removing a vascular occlusion according to the invention.

It is suitable for use to remove a vascular occlusion 10a and, preferably, a chronic occlusion from a blood vessel 10 and, preferably, from a coronary artery.

The removal device 1 comprises a first guide wire 2 suitable to be inserted into the blood vessel 10 and placed so as to correspond with the vascular occlusion 10a via retrograde approach; a guiding member 3 suitable to control the first guide wire 2 during the passage through the vascular occlusion 10*a*; a second guide wire 4 suitable to permit the guiding member 3 to be placed inside the blood vessel 10 in correspondence with the vascular occlusion 10*a* and, in particular, via anterograde approach and from the opposite side with respect to the first guide wire 2; and at least one hollow tube 5 suitable to permit the insertion and movement of the guide wires 2 and 4 and the guiding element 3 inside the blood vessel 10.

In particular, the hollow tubes 5, of a type that is known, are two in number and consist of catheters or other similar elements suitable to be inserted into a blood vessel 10 and having an internal cavity through which the guide wires 2 and 4 and the guiding element 3 can be inserted into the blood vessel 10.

The guide wires 2 and 4 are inserted inside the tubes 5.

The guide wires 2 and 4 consist of an element suitable to slide within a blood vessel 10 so as to reach the vascular occlusion 10*a*. They may therefore consist of a wire made of flexible, atraumatic material, which must penetrate the coronary lumen and act as a "guide", like a track, for the passage of the other materials, such as, for example, the member 3. For example, they are made of a metal alloy and possibly coated.

Each of the wires 2 and 4 thus consists of a tubular-shaped element having a practically constant and circular cross-section characterised by a diameter that is substantially less than 0.1 inches (2.54 mm), in particular, substantially less than 0.05 inches (1.27 mm) and, preferably, substantially equal to 0.014 inches (0.36 mm), 0.018 inches (0.46 mm) or, alternatively, 0.035 inches (0.89 mm).

Furthermore, the first guide wire 2, advantageously has at least the head 2*a*, i.e., the portion of the wire 2 suitable to be arranged in proximity to the occlusion 10*a*, at least partially made of ferromagnetic material, that is to say materials suitable to interact with a magnetic field so as to allow the guiding member 3, as explained more fully below, to exert at least a restoring force on said head 2*a* and thus guide the motion of the first guide wire 2 as it passes through the vascular occlusion 10*a*.

For that purpose, the head 2*a* has a central body made of ferromagnetic material, for example iron, nickel, cobalt, manganese, neodymium, boron, etc. or of an alloy containing one or more of said chemical elements, and which, to guarantee smoothness and for hygiene and health reasons, is appropriately coated in a hydrophilic or hydrophobic polymer like the rest of the first guide wire 2.

Alternatively the head 2*a* may be electromagnetic, i.e. suitable not only for reacting to a magnetic field but also for generating its own magnetic field.

Unlike the first wire 2, the second guide wire 4 is almost totally made of austenitic steel, polypropylene or other non-magnetic material which therefore has no appreciable magnetic properties, i.e., which is characterised by a relative magnetic permeability of very close to one so as not to be affected by the influx of the magnetic field emitted by the guiding member 3.

The guiding member 3 comprises an emitter 3*a* suitable to emit the magnetic field interacting with the head 2*a* of the first guide wire 2 and a coating 3*b* suitable to cover the emitter 3*a* so as to prevent it from coming into contact with the vessel 10.

In particular, the coating 3*b* comprises a first portion covering the emitter 3*a* and a second portion suitable to engage with the second wire 4 so that the operator is able to control the sliding thereof along the second guide wire 4. In particular, said second portion may consist of a tube appropriately counter-shaped with respect to the second wire 4 and, thus, having an internal cavity with a diameter that is substantially less than 5 mm and, preferably, substantially less than 2 mm.

Like the coating 3*b*, the emitter 3*a*, since it must slide along the second guide wire 4, consists of a body provided with a hooking cavity suitable to engage with the second guide wire 4 and, thus, with dimensions that substantially coincide with those of the cavity of the coating 3*b*.

Moreover, in order to achieve optimal sliding within the blood vessel 10, the emitter 3*b* is cylindrical, ogival or spherical in shape or of another similar shape, or may consist of several members arranged in series, contiguous to one another and detached so as also to be able to follow tight bends and so as to facilitate the movement of the emitter.

It consists of a permanent magnet, that is, an element which emits a magnetic field with a strength that is practically constant, without the need for external stimulation. In particular, the emitter 3*a* consists of a ferromagnetic material, that is, a material that can become highly magnetised under the action of an external magnetic field and continue to be magnetised for a long time when the external magnetic field is removed, thus in turn becoming a magnet itself. More in particular, it may consist of a neodymium-iron-boron alloy and, preferably, of a tetragonal crystalline Nd2Fe14B alloy.

Alternatively, the emitter 3*a* is an electromagnet, that is an element which, unlike a permanent magnet, is only capable of emitting a magnetic field when subjected to an external stimulation and, more precisely, only when electrically powered. It therefore consists of a coil, a solenoid or other element comprising a conducting wire and which acts as a magnet when an electric current passes through it, but which stops emitting the magnetic field when no current passes through it.

Lastly, in some cases the emitter 3*a* may consist of a coil/solenoid wound around a ferromagnetic core, for example steel, to increase the magnetic field that is produced.

In the case of the emitter 3*a* consisting of an electromagnet, the guiding member 3 is also provided with electrical connection means 3*c* suitable to connect the emitter 3*a* to a battery, an external electrical power supply mains or other power supply, not illustrated in the figure, suitable to supply direct or alternating current or current with different particular waveforms to the emitter 3*a*.

In particular, the power supply is suitable to remain outside the patient and the connection means 3*c* therefore consist of electrical wires suitable to be inserted into the blood vessel 10 via the tube 5, through which the second guide wire 4 is inserted or via a supplementary tube. Alternatively, the guiding means 3 consist of wires appropriately integrated into the coating 3*b*.

The functioning of the device for removing a vascular occlusion described above in a structural sense, is as follows.

First, the operator injects a contrast medium into the patient and performs radiography on the area concerned in order to display the image on a screen.

Next, the operator arranges the hollow tubes 5 in the correct working position, inserting them inside the patient's body through specific punctures or incisions performed on the patient 5. The operator then inserts the first guide wire 2 through one of the tubes 5 into the blood vessel 10 using, for example, a retrograde approach to place it in proximity to the occlusion 10*a*, as shown in FIG. 2*a*.

In particular, once the first wire 2 has reached the occlusion 10a, the operator uses the tapered section to insert the head 2a inside the vascular occlusion 10a so as to block the first wire 2 in the desired position. When this operation is complete, the operator inserts the second guide wire 4 into the vessel 10 through the other tube 5 (FIG. 2b), advancing until it reaches the occlusion 10a from the opposite side with respect to the first wire 2.

When this position has been reached, the operator engages the guiding member 3 in the second guide wire 4 and then slides it along said second guide wire 4 until the emitter 3a reaches the occlusion 10a and, in particular, so as to bring the emitter 3a substantially into contact with the occlusion 10a, as shown in FIG. 2c.

Next the operator activates the emitter 3a so that it starts to emit a magnetic field, and then moves the first guide wire 2 to make it pass through the occlusion 10a, as illustrated in FIGS. 2d and 2e.

During this procedure the magnetic field produced by the emitter 3a, interacting with the head 2a, generates a force on the first guide wire 2 that pushes the head 2a and, thus, the wire 2 against said emitter 3a. In particular, owing to the fact that the head 2a and the emitter 3a are arranged on reciprocally opposite sides with respect to the occlusion 10a, said force is exerted in a direction passing through the occlusion 10a and so pushes the first guide wire 2 through the occlusion 10a until it comes into contact with the emitter 3a.

In detail, the emitter 3a, if consisting of an electromagnet and powered by an alternating current, emits a variable magnetic field with a polarity that changes in time and, thus, subjects the head 2a to a force which, exerted in a constant direction but with varying intensity and polarity, alternately attracts the head 3a, if the polarities are opposite, or repels it, if the polarities are the same. As a result of said variation in the force, the head 2a passes through the occlusion 10a with an oscillatory motion and, thus, acquires a vibratory or oscillatory motion which facilitates its penetration of the material occluding the vessel.

Once the head 2a comes into contact with the guiding member 3, the operator proceeds to use a balloon or other similar means of expansion which is mounted on and made to slide along the first guide wire 2 until reaching the vascular occlusion 10a, which is inflated so as to re-establish a normal blood flow in the blood vessel 10. Alternatively, the operator may recover the wire 2 in the tubular element 5 and proceed with the dilation of the occlusion via anterograde.

The invention achieves some important advantages.

A first important advantage, obtained thanks to the removal device 1, consists of the extreme simplicity and speed with which an operation to remove a vascular occlusion 10a can be performed.

Said advantage is achieved thanks to the emitter 3a which, since it is positioned in the blood vessel 10 in correspondence with the occlusion 10a, enables the first guide wire 2 to be guided as it passes through the vascular occlusion 10a. In particular, the restoring force applied by the emitter 3a to the head 2a, facilitates the passage of the first guide wire 2 through the occlusion 10a and thus prevents the first wire 2 from damaging the blood vessel 10, which can give rise to periprocedural complications.

Moreover, owing to the advantageous force applied by the emitter 3a to the head 2a, the operator can apply less force to the first guide wire 2 as it passes through the occlusion 10 and, thus, move said first guide wire 2 more easily and quickly.

A further advantage, achieved thanks to said speed of intervention, lies in the fact that with the removal device 1, it is possible to reduce the exposure time to radiation and the amount of contrast medium injected into the patient with respect to when using the removal devices known in the prior art.

A further advantage therefore consists of the fact that operations using the innovative removal device 1 can be performed at a lower cost.

Modifications and variations may be made to the invention described herein without departing from the scope of the inventive concept. All the elements as described and claimed herein may be replaced with equivalent elements and the scope of the invention includes all other details, materials, shapes and dimensions.

The invention claimed is:

1. A removal device for removing a vascular occlusion, comprising:
no more than one emitter configured to emit a magnetic field;
a first guide wire configured to be inserted into a blood vessel in correspondence with said vascular occlusion, said first guide wire comprising at least a head made of ferromagnetic material so that said emitter is able to exert a restoring force on said first guide wire;
a non-magnetic second guide wire configured to permit said emitter to be placed inside said blood vessel in correspondence with said vascular occlusion and on an opposite side with respect to said first guide wire;
wherein said emitter is provided with a cavity configured to permit said emitter to engage with said second guide wire so as to slide along the whole said second guide wire, and
wherein said emitter is configured to move the first guide wire to make it pass through the occlusion.

2. The removal device as claimed in claim 1, wherein said emitter comprises a permanent magnet.

3. The removal device as claimed in claim 2, wherein said emitter consists of a neodymium-iron-boron alloy.

4. The removal device as claimed in claim 3, wherein the neodymium-iron-boron alloy is a tetragonal crystalline Nd2Fe14B alloy.

5. The removal device as claimed in claim 2, further comprising a coating configured to enclose said emitter.

6. The removal device as claimed in claim 1, wherein said emitter is an electromagnetic emitter configured to emit said magnetic field when electrically powered.

7. The removal device as claimed in claim 6, further comprising electrical connection means configured to connect said emitter to a power supply.

* * * * *